US012746057B2

(12) United States Patent
Takahashi

(10) Patent No.: US 12,746,057 B2
(45) Date of Patent: Sep. 29, 2026

(54) MEDICAL DEVICE

(71) Applicant: TERUMO KABUSHIKI KAISHA, Tokyo (JP)

(72) Inventor: Yusuke Takahashi, Hadano (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 936 days.

(21) Appl. No.: 17/704,544

(22) Filed: Mar. 25, 2022

(65) Prior Publication Data

US 2022/0211432 A1 Jul. 7, 2022

Related U.S. Application Data

(63) Continuation of application No. PCT/JP2020/036815, filed on Sep. 29, 2020.

(30) Foreign Application Priority Data

Sep. 30, 2019 (JP) ................................ 2019-179477

(51) Int. Cl.
*A61B 18/14* (2006.01)
*A61B 18/00* (2006.01)

(52) U.S. Cl.
CPC .. *A61B 18/1492* (2013.01); *A61B 2018/0016* (2013.01); *A61B 2018/00267* (2013.01);
(Continued)

(58) Field of Classification Search
CPC .. A61B 2018/00267; A61B 2018/0016; A61B 18/1492
See application file for complete search history.

(56) References Cited

U.S. PATENT DOCUMENTS 9,615,848 B2 4/2017 Pigott
2007/0083194 A1* 4/2007 Kunis ................ A61B 18/1492
606/41

(Continued)

FOREIGN PATENT DOCUMENTS

JP 2005270394 A 10/2005
JP 2018023840 A 2/2018

(Continued)

OTHER PUBLICATIONS

International Search Report (PCT/ISA/210) with translation and Written Opinion (PCT/ISA/237) mailed on Dec. 1, 2020, by the Japanese Patent Office as the International Searching Authority for International Application No. PCT/JP2020/036815. (10 pages).

*Primary Examiner* — Linda C Dvorak
*Assistant Examiner* — Ryan T Clark
(74) *Attorney, Agent, or Firm* — BUCHANAN INGERSOLL & ROONEY PC

(57) ABSTRACT

A medical device includes an elongate shaft and an expansion body at a distal portion of the shaft portion. The shaft includes an outer tube, and an inner tube that is slidable inside the outer tube. The expansion body includes a first connecting portion connected to the outer tube, and a second connecting portion connected to the inner tube. The outer tube includes an open end where an opening portion is formed, and the inner tube enters/exits from the opening portion. The expansion body is settable to a reference form where the expansion body is radially widened, and is settable to a contracted form where the expansion body is radially contracted. In the reference form, the open end is between the first and second connecting portions, and when the expansion body is deformed from the reference form into the contracted form, the inner tube is extracted from the opening portion.

23 Claims, 7 Drawing Sheets

(52) U.S. Cl.
CPC ............... *A61B 2018/00351* (2013.01); *A61B 2018/00577* (2013.01)

(56) References Cited

U.S. PATENT DOCUMENTS

| | | | |
|---|---|---|---|
| 2010/0312338 A1 | 12/2010 | Gonzales et al. | |
| 2015/0119862 A1* | 4/2015 | Cajamarca ........ | A61M 25/0045 29/424 |
| 2017/0080195 A1 | 3/2017 | Dosono | |
| 2018/0161577 A1* | 6/2018 | Goedeke ................ | A61B 5/349 |
| 2019/0151615 A1 | 5/2019 | Kitaoka et al. | |
| 2020/0138445 A1 | 5/2020 | Takahashi et al. | |

FOREIGN PATENT DOCUMENTS

| | | | |
|---|---|---|---|
| WO | 2015186626 | A1 | 12/2015 |
| WO | 2018016529 | A1 | 1/2018 |
| WO | 2019009254 | A1 | 1/2019 |
| WO | 2019181634 | A1 | 9/2019 |

* cited by examiner

Fig. 10(A)
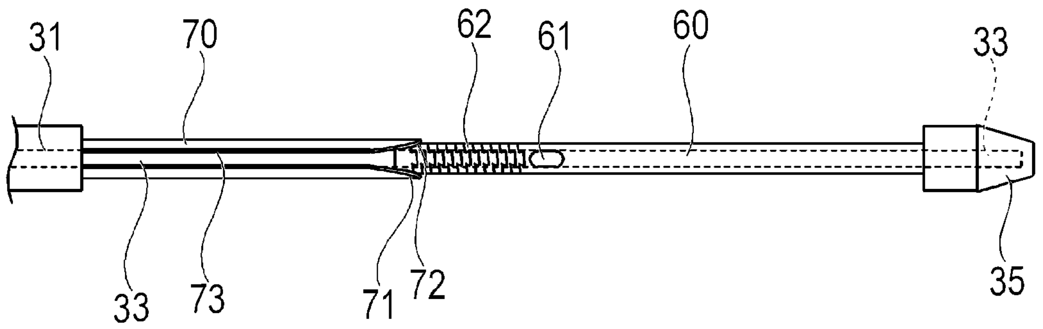
Fig. 10(B)
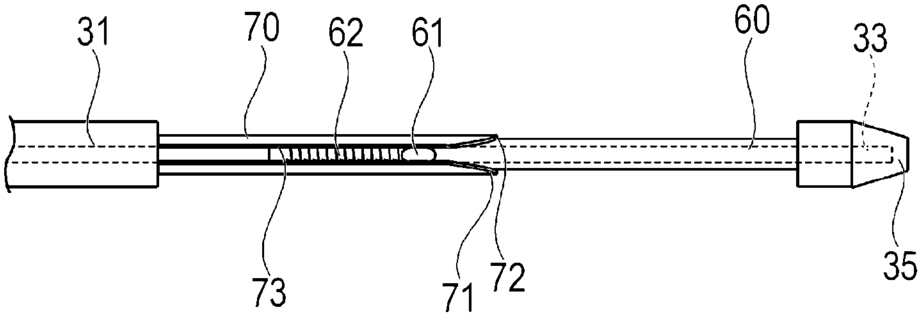
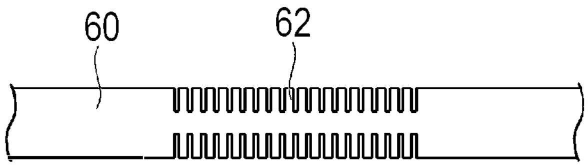
Fig. 11(A)
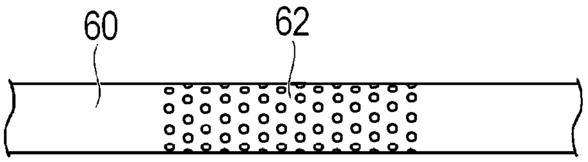
Fig. 11(B)
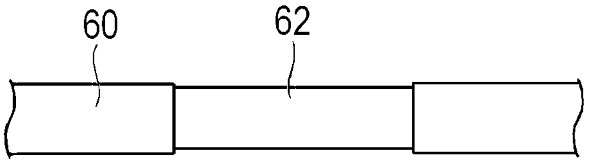
Fig. 11(C)
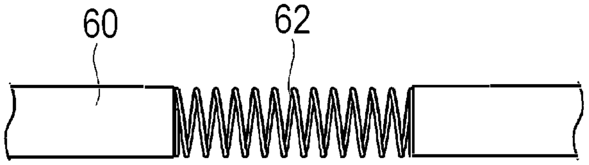
Fig. 11(D)
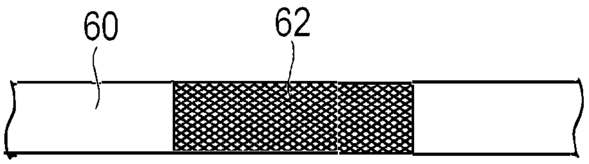
Fig. 11(E)

MEDICAL DEVICE

CROSS-REFERENCES TO RELATED APPLICATIONS

This application is a continuation of International Patent Application No. PCT/JP2020/036815 filed on Sep. 29, 2020, which claims priority to Japanese Patent Application No. 2019-179477 filed on Sep. 30, 2019, the entire content of both of which is incorporated herein by reference.

TECHNOLOGICAL FIELD

The present invention generally relates to a medical device that expands and maintains a hole in biological tissue, and a treatment method involving expanding and maintaining a hole in biological tissue.

BACKGROUND DISCUSSION

Chronic heart failure is one of several known heart diseases. Chronic heart failure is broadly classified into a systolic heart failure and a diastolic heart failure, based on a cardiac function index. In a patient suffering from the diastolic heart failure, a myocardium is hypertrophied and increases in stiffness (hardness), so that the blood pressure in a left atrium increases and the pumping function of a heart is decreased. Accordingly, the patient shows a heart failure symptom such as a pulmonary edema. There is also a heart disease in which the blood pressure on a right atrium side increases due to pulmonary hypertension or the like, and the pumping function of a heart is decreased, thereby showing heart failure symptoms.

In recent years, for patients suffering from a heart failure, attention has been paid to a shunt treatment in which a shunt (through-hole) serving as an escape route for increased atrial pressure is formed in an atrial septum, thereby being able to reduce heart failure symptoms. In the shunt treatment, the atrial septum is accessed using a transvenous approach method, and a through-hole is formed. Then, a method has been known in which a through-hole is widened to a desired size and the through-hole is subjected to energy and cauterized, to form a shunt hole.

In addition, a method for widening a formed hole in a biological lumen is performed in cases other than the case of forming a shunt hole in the atrial septum. For example, Japanese Patent Application Publication No. 2018-23840 discloses a device that cuts and widens a blood vessel that is narrowed by arterioscleosis. In the device, an outer shaft is fixed to proximal portions of a plurality of expandable portions extending in an axial direction at a distal portion of the device, and an inner shaft penetrating through the outer shaft is fixed to distal portions of the plurality of expandable portions. Therefore, when the inner shaft is pulled to a proximal side with respect to the outer shaft, a compression force acts on the expandable portions, and the expandable portions are expanded to bend outward in a radial direction.

SUMMARY

In the device disclosed in Japanese Patent Application Publication No. 2018-23840, when the inner shaft is pulled to expand the expandable portions, the inner shaft may be bent, and a central axis of the expandable portions and a pulling axis of the inner shaft may be displaced from each other. In this case, the plurality of expandable portions arranged in a circumferential direction are not uniform, and an expansion force of the expandable portions is not uniform. Accordingly, the expansion force may be decreased, or a hole in a living body may be not expandable to a desired shape.

On the other hand, when a tube side shaft to be pulled so as to expand the expandable portions is made rigid, since the device is difficult to bend, the passability of the device in a delivery sheath that allows the device to reach a target site, or in a biological lumen such as a blood vessel is decreased.

The medical device disclosed here exhibits improved passability in a tubular member or in a biological lumen, and suppressing a decrease in expansion force to widen a biological tissue.

According to one aspect, there is provided a medical device including: a shaft portion that is elongate; and an expansion body provided at a distal portion of the shaft portion to be expandable and contractable in a radial direction. The shaft portion includes an outer tube, and an inner tube that is slidable in an axial direction inside the outer tube. The expansion body includes a first connecting portion connected to the outer tube, and a second connecting portion connected to the inner tube. The outer tube includes an opening end at which an opening portion is formed, the inner tube entering and exiting from the opening portion. The expansion body is settable to a reference form where the expansion body is widened in the radial direction in a natural state, and is settable to a contracted form where the expansion body is contracted in the radial direction, when the first connecting portion and the second connecting portion are more separated from each other than in the reference form. In the reference form, the opening end is located between the first connecting portion and the second connecting portion, and when the expansion body is deformed from the reference form into the contracted form, a part of the inner tube is extracted from the opening portion.

In the medical device configured as described above, in the contracted form where the inner tube is extracted from the outer tube, a range where the outer tube and the inner tube overlap each other between the first connecting portion and the second connecting portion is shortened. For this reason, in the contracted form where the expansion body is contracted, the flexibility of the medical device between the first connecting portion and the second connecting portion is improved, and the passability of the medical device in a tubular member such as a sheath or in a biological lumen is improved. In addition, in the medical device, in the reference form where the expansion body is expanded, the range where the outer tube and the inner tube overlap each other between the first connecting portion and the second connecting portion is lengthened. For this reason, in the medical device, the shaft portion is difficult to bend between the first connecting portion and the second connecting portion. For this reason, the medical device can maintain the expansion body in a proper shape in the reference form, so that a decrease in expansion force can be suppressed.

The expansion body may be settable to an expanded form where the expansion body is expanded in the radial direction, when the first connecting portion and the second connecting portion approach each other from the reference form, and when the expansion body is deformed from the reference form into the expanded form, a part of the inner tube may be stored inside the outer tube from the opening portion. Accordingly, even when a compression force is acted on the expansion body in the axial direction to set the expansion body to the expanded form where the expansion body is more expanded in the radial direction than in the reference form, the shaft portion is difficult to bend between the first connecting portion and the second connecting portion, so that buckling can be suppressed. For this reason, in the medical device, the expansion body is settable to the expanded form of a desired shape that is uniform in a circumferential direction, so that a decrease in expansion force can be suppressed and a biological tissue can be uniformly widened in the radial direction.

The outer tube and/or the inner tube may include a flexible portion having lower flexural rigidity than a portion adjacent to the flexible portion in the axial direction. In the reference form, the flexible portion may be located in a range where the outer tube and the inner tube overlap each other. In the contracted form, the flexible portion may be located in a range different from the range where the outer tube and the inner tube overlap each other. Accordingly, in the contracted form, the flexible portion is located outside the range where the outer tube and the inner tube overlap each other, so that the flexible portion can be flexibly bent. For this reason, in the contracted form, the flexibility of the medical device between the first connecting portion and the second connecting portion is improved, and the passability of the medical device in a tubular member such as a sheath or in a biological lumen is improved. In addition, in the reference form, since the flexible portion is located in the range where the outer tube and the inner tube overlap each other, the medical device is difficult to bend between the first connecting portion and the second connecting portion. Therefore, the medical device can maintain the expansion body in a proper shape in the reference form, so that a decrease in expansion force can be suppressed and a biological tissue can be uniformly widened in the radial direction.

The outer tube may include a first engagement portion. The inner tube may include a second engagement portion. At least in the reference form, the first engagement portion and the second engagement portion may be slidable in the axial direction, and come into contact with each other in a circumferential direction to limit relative rotation between the outer tube and the inner tube. Accordingly, at least in the reference form, relative rotation between the outer tube and the inner tube is limited. For this reason, at least in the reference form, the twisting of the expansion body can be suppressed. Therefore, in the medical device, the expansion body is settable to the reference form of a desired shape, and a decrease in expansion force can be suppressed.

A flexible portion may be formed of a slit portion having a spiral shape or a groove provided in the outer tube and/or in the inner tube. Accordingly, the flexible portion of the outer tube and/or the inner tube can be flexibly bent and easily processed.

A flexible portion may be formed of a plurality of wires. Accordingly, the flexible portion of the outer tube and/or the inner tube can be flexibly bent.

A flexible portion may be formed in a coil shape. Accordingly, the flexible portion of the outer tube and/or the inner tube can be flexibly bent.

A flexible portion may be made of a material softer than a material of a portion adjacent to the flexible portion in the axial direction. Accordingly, the flexible portion of the outer tube and/or the inner tube can be flexibly bent.

In addition, according to another aspect, there is provided a medical device including: a shaft portion that is elongate. The shaft portion may include an outer tube, and an inner tube that is slidable in an axial direction inside the outer tube. The outer tube may include an opening end at which an opening portion is formed, the inner tube entering and exiting from the opening portion. The shaft portion may be settable to an accommodated form where at least a part of the inner tube is accommodated in the outer tube, and may be settable to an extended form where the inner tube is extracted from the opening portion from the accommodated form. The outer tube and/or the inner tube may include a flexible portion having lower flexural rigidity than a portion adjacent to the flexible portion in the axial direction. In the accommodated form, the flexible portion may be located in a range where the outer tube and the inner tube overlap each other. In the extended form, the flexible portion may be located in a range different from the range where the outer tube and the inner tube overlap each other.

Accordingly, in the extended form, the flexible portion is located outside the range where the outer tube and the inner tube overlap each other, so that the flexible portion can be flexibly bent. For this reason, in the extended form, the flexibility of the medical device is improved, and the passability of the medical device in a tubular member such as a sheath or in a biological lumen is improved. In addition, in the accommodated form, the flexible portion is located in the range where the outer tube and the inner tube overlap each other. For this reason, in the accommodated form, it is possible to make the medical device difficult to bend.

According to another aspect, a treatment method to widen a through-hole in biological tissue comprises introducing an expansion body into the through-hole in the biological tissue so that the expansion body is positioned in the through hole. The expansion body includes a first connecting portion connected to an outer tube and a second connecting portion connected to an inner tube, with the inner tube being axially movable relative to the outer tube, and the outer tube includes an extending portion that extends from the first connecting portion and is located inwardly of the expansion body, with the extending portion of the outer tube having a distal open end. The introducing of the expansion body into the through-hole in the biological tissue occurs while the expansion body is in a contracted form and while a proximal portion of the inner tube extends from the distal open end of the extending portion of the outer tube. The treatment method may further involve radially outwardly widening the through-hole in the biological tissue by radially outwardly expanding the expansion body, wherein the radially outward expanding of the expansion body includes moving the first connecting portion and the second connecting portion towards one another while moving the proximal portion of the inner tube into the extending portion of the outer tube so that an axial distance between the first connecting portion and the second connecting portion when the expansion body is in the contracted state and is introduced into the through-hole in the biological tissue is greater than the axial distance between the first connecting portion and the second connecting portion when the expansion body is radially outwardly expanded during the radially outward widening of the through-hole in the biological tissue.

BRIEF DESCRIPTION OF THE DRAWINGS

FIG. 3(A) illustrates a contracted form where the expansion body is contracted, FIG. 3(B) illustrates a reference form where the expansion body is in an original shape, and FIG. 3(C) illustrates an expanded form where the expansion body is expanded.

FIG. 8(A) illustrates a contracted form, and FIG. 8(B) illustrates a reference form.

FIG. 9(A) illustrates a contracted form, and FIG. 9(B) illustrates a reference form.

FIGS. 10(A) and 10(B) illustrate plan views of the vicinity of an outer tube and an inner tube of a medical device according to a third modification example, FIG. 10(A) illustrates an extended form, and FIG. 10(B) illustrates an accommodated form.

FIGS. 11(A)-11(E) illustrate plan views of the vicinities of flexible portions of modification examples in a medical device, FIG. 11(A) illustrates a fourth modification example, FIG. 11(B) illustrates a fifth modification example, FIG. 11(C) illustrates a sixth modification example, FIG. 11(D) illustrates a seventh modification example, and FIG. 11(E) illustrates an eighth modification example.

DETAILED DESCRIPTION

Figure 1:
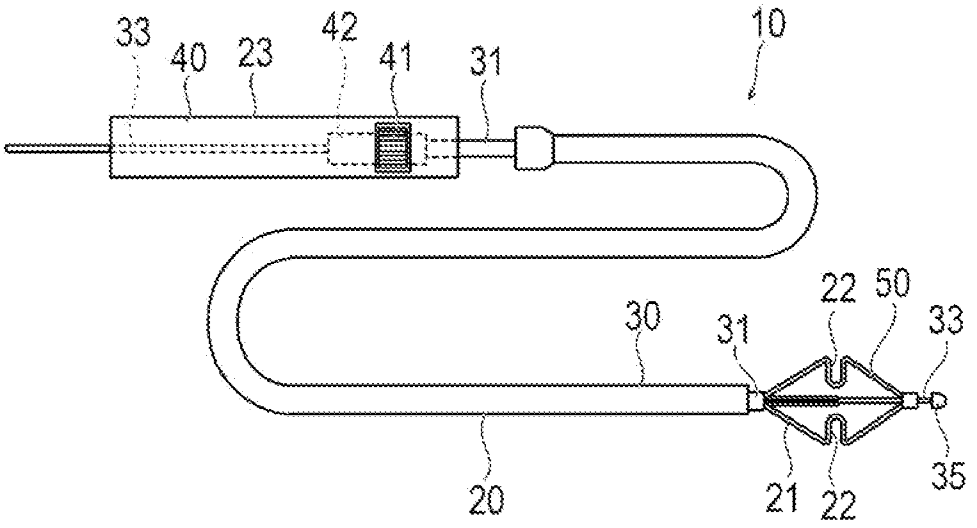
FIG. 1 is a front view illustrating an overall configuration of a medical device according to the present embodiment.

Set forth below with reference to the accompanying drawings is a detailed description of embodiments of a medical device representing examples of the medical device disclosed here. The dimensions or scales on the drawings may be exaggerated or different from actuality/reality for convenience of description and illustration. Dimensional ratios in the drawings may be exaggerated and different from actual ratios for convenience of description. In addition, in the specification, a side on which a medical device 10 is inserted into a biological lumen is referred to as a "distal side", and a side on which operation is performed is referred to as a "proximal side".

Figure 4:
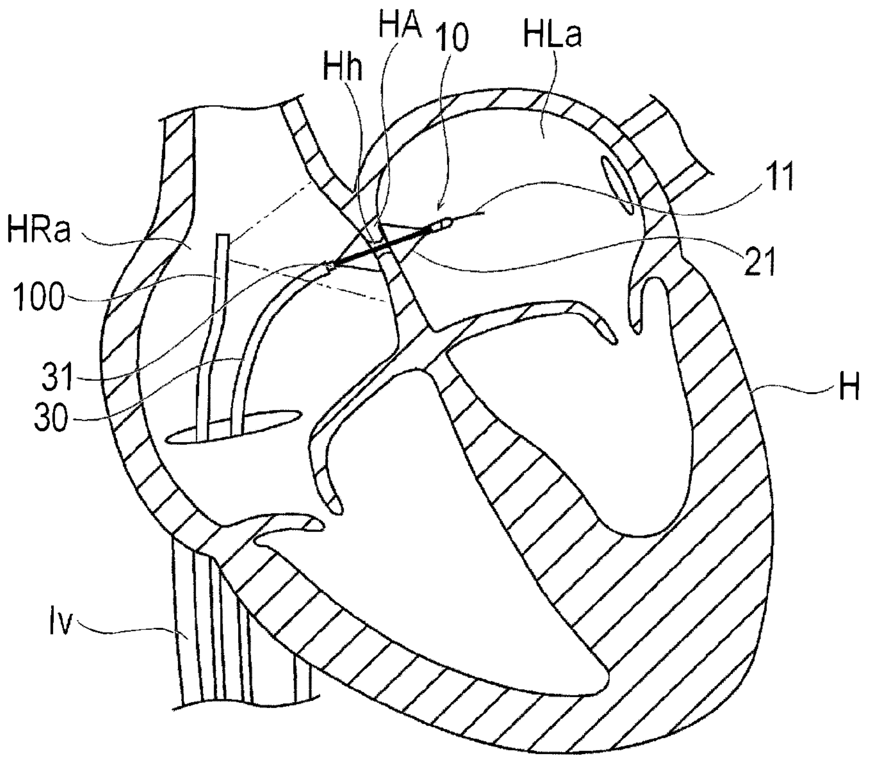
FIG. 4 is a view for describing a treatment method using the medical device according to the present embodiment, and is a view for schematically describing a state where the expansion body is disposed in a through-hole of an atrial septum, in which the medical device and a biological tissue are illustrated in a front view and in a cross-sectional view, respectively.

As illustrated in FIG. 4, the medical device 10 according to the present embodiment is configured to be able to expand a through-hole Hh formed in an atrial septum HA of a heart H of a patient and to perform maintenance treatment to maintain the size of the expanded through-hole Hh.

Figure 2:
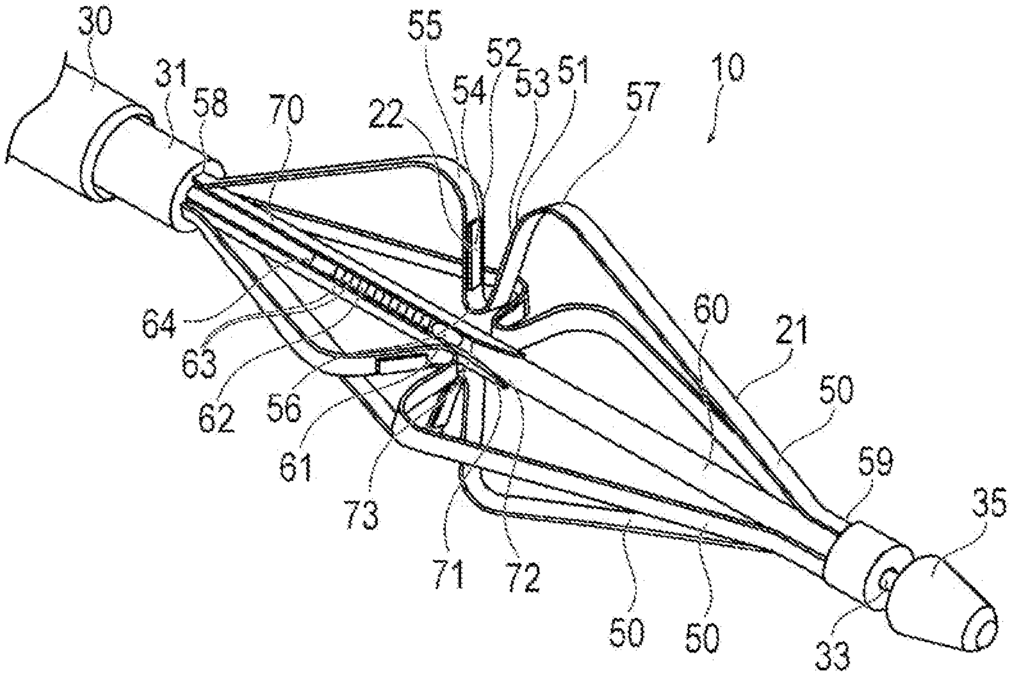
FIG. 2 is an enlarged perspective view of the vicinity of an expansion body.

As illustrated in FIGS. 1 and 2, the medical device 10 of the present embodiment includes a shaft portion 20 that is elongate (elongated), an expansion body 21 provided at a distal portion of the shaft portion 20, a pulling shaft 33 that expands the expansion body 21, and an operation unit 23 provided at a proximal portion of the shaft portion 20. The expansion body 21 is provided with an energy transmission element 22 for performing the aforementioned maintenance treatment.

The shaft portion 20 includes a main shaft 31 that holds the expansion body 21 at a distal portion of the main shaft 31, a storage sheath 30 that stores the main shaft 31, an outer tube 70 connected to the distal portion of the main shaft 31, and an inner tube 60 that can be stored in the outer tube 70. The storage sheath 30 is movable forward and backward with respect to the main shaft 31 in an axial direction. In a state where the storage sheath 30 is moved to a distal side or in the distal (forward) direction of the shaft portion 20, the storage sheath 30 can store the expansion body 21 thereinside. The storage sheath 30 is moved to the proximal side or in the proximal direction from a state where the expansion body 21 is stored, and thus the expansion body 21 can be exposed.

A proximal portion of the main shaft 31 is connected to the operation unit 23. The distal portion of the main shaft 31 is connected to a proximal portion of the expansion body 21 and to a proximal portion of the outer tube 70. The outer tube 70 extends to the distal side from the distal portion of the main shaft 31. That is, the outer tube 70 extends distally beyond the distal portion of the main shaft 31.

The pulling shaft 33 is stored inside the main shaft 31, the outer tube 70, and the inner tube 60. The pulling shaft 33 is a shaft for pulling to apply a compression force on the expansion body 21. An axially orthogonal cross section of an outer peripheral surface of the pulling shaft 33 is a substantially circular shape. The pulling shaft 33 protrudes from a distal end of the inner tube 60 to the distal side, and a distal portion of the pulling shaft 33 is connected to a distal member 35. A proximal portion of the pulling shaft 33 extends out to the proximal side or in the proximal direction from the operation unit 23 as shown in FIG. 1. The distal member 35 to which the distal portion of the pulling shaft 33 is fixed may not be fixed to the expansion body 21. Accordingly, the distal member 35 can pull the expansion body 21 in a compression direction. In addition, when the expansion body 21 is stored in the storage sheath 30, the distal member 35 is separated to the distal side from the expansion body 21, so that the expansion body 21 can be easily moved in a stretching direction and storability can be improved.

The operation unit 23 includes a housing 40 to be gripped by an operator, an operation dial 41 to be rotationally operable by the operator, and a conversion mechanism 42 that operates in conjunction with rotation of the operation dial 41. The pulling shaft 33 is held by the conversion mechanism 42 inside the operation unit 23. The conversion mechanism 42 can move the held pulling shaft 33 forward and backward along the axial direction with rotation of the operation dial 41. For example, a rack and pinion mechanism can be used as the conversion mechanism 42.

As illustrated in FIG. 2, the expansion body 21 includes a plurality of wire portions 50 arranged or spaced apart from one another in a circumferential direction. In the present embodiment, four wire portions 50 are provided in the circumferential direction. The number of the wire portions 50 is not particularly limited. Each of the wire portions 50 is expandable and contractable in a radial direction of the expansion body 21. A proximal portion of the wire portion 50 is connected to a first connecting portion 58 provided at the distal portion of the main shaft 31. The first connecting portion 58 located at the proximal portion of the wire portion 50 is connected to the proximal portion of the inner tube 60 and to the distal portion of the main shaft 31. A second connecting portion 59 located at a distal portion of the wire portion 50 is connected to a distal portion of the inner tube 60. The distal portion of the wire portion 50 extends from the distal portion of the inner tube 60 to the proximal side or in the proximal direction. The wire portion 50 is inclined such that the size in the radial direction increases from both end portions toward a central portion in the axial direction. In addition, the wire portion 50 includes a holding portion 51 having a valley shape in the radial direction of the expansion body 21, at the central portion of the wire portion 50 in the axial direction.

The holding portion 51 includes a proximal side holding portion 52, and a distal side holding portion 53 located closer to the distal side than the proximal side holding portion 52. That is, the distal side holding portion 53 is distal of the proximal side holding portion 52. The holding portion 51 further includes a proximal side outward projection portion 55, an inward projection portion 56, and a distal side outward projection portion 57. It is preferable that an interval between the proximal side holding portion 52 and the distal side holding portion 53 in the axial direction is slightly wider on a radially outward side than on a radially inward side, in a natural state where no external force acts thereon. Accordingly, a biological tissue is easily disposed between the proximal side holding portion 52 and the distal side holding portion 53 from the radially outward side.

The proximal side holding portion 52 includes a projection portion 54 protruding toward the distal side. The energy transmission element 22 is disposed on the projection portion 54. The proximal side holding portion 52 may not include the projection portion 54. Namely, the energy transmission element 22 may not protrude to the distal side.

The proximal side outward projection portion 55 is located on a proximal side of the proximal side holding portion 52, and is formed in a shape projecting outward in the radial direction. The distal side outward projection portion 57 is located on a distal side of the distal side holding portion 53, and is formed in a shape projecting outward in the radial direction. The inward projection portion 56 is located between the proximal side holding portion 52 and the distal side holding portion 53, and is formed in a shape projecting inward in the radial direction. The proximal side outward projection portion 55, the inward projection portion 56, and the distal side outward projection portion 57 are stored in the storage sheath 30, thus being deformable from a projection shape into a shape close to being flat.

In the present embodiment, the energy transmission element 22 is provided at the proximal side holding portion 52, but the energy transmission element 22 may be provided at the distal side holding portion 53.

Each of the wire portions 50 forming the expansion body 21 has, for example, a flat plate shape obtained by cutting a cylinder. A wire forming the expansion body 21 can have a thickness of 50 to 500 μm and a width of 0.3 to 2.0 mm. However, a wire forming the expansion body 21 may have dimensions outside these ranges. In addition, the shape of the wire portion 50 is not limited, and may have, for example, a circular cross-sectional shape or other cross-sectional shapes.

Since the energy transmission element 22 is provided at the projection portion 54 of the proximal side holding portion 52, when the holding portion 51 holds the atrial septum HA, energy from the energy transmission element 22 is transmitted from a right atrium side to the atrial septum HA. When the energy transmission element 22 is provided at the distal side holding portion 53, energy from the energy transmission element 22 is transmitted from a left atrium side to the atrial septum HA.

The energy transmission element 22 is configured as, for example, a bipolar electrode that receives electric energy from an energy supply device (not illustrated) that is an external device. In this case, energization is performed between the energy transmission elements 22 disposed on the wire portions 50. The energy transmission element 22 and the energy supply device are connected to each other by a conducting wire (not illustrated) coated with an insulating coating material. The conducting wire is led out to the outside via the shaft portion 20 and via the operation unit 23, and is connected to the energy supply device.

Alternatively, the energy transmission element 22 may be configured as a monopolar electrode. In this case, energization is performed between the energy transmission element 22 and a counter electrode plate prepared outside a body. In addition, the energy transmission element 22 may be a heating element (electrode chip) that receives high-frequency electric energy from the energy supply device to generate heat. In this case, energization is performed between the energy transmission elements 22 disposed on the wire portions 50. Further, the energy transmission element 22 can be configured as an element capable of applying energy to the through-hole Hh, such as an element that exerts a heating or cooling action using microwave energy, ultrasound energy, coherent light such as laser, a heated fluid, a cooled fluid, or a chemical medium, an element that generates frictional heat, or a heater including an electric wire or the like, and a specific form of the energy transmission element 22 is not particularly limited.

The wire portion 50 can be made of a metallic material. As the metallic material, for example, a titanium-based (Ti—Ni, Ti—Pd, Ti—Nb—Sn, or the like) alloy, a copper-based alloy, stainless steel, β-titanium steel, or a Co—Cr alloy can be used. It is better to use an alloy or the like having a spring property such as a nickel-titanium alloy. However, the material for the wire portion 50 is not limited to these materials, and the wire portion 50 may be made of other materials.

The pulling shaft 33 is stored inside the shaft portion 20. A guide wire lumen is formed in the pulling shaft 33 and in the distal member 35 along the axial direction, and a guide wire 11 can be inserted into the guide wire lumen.

Figure 3A:
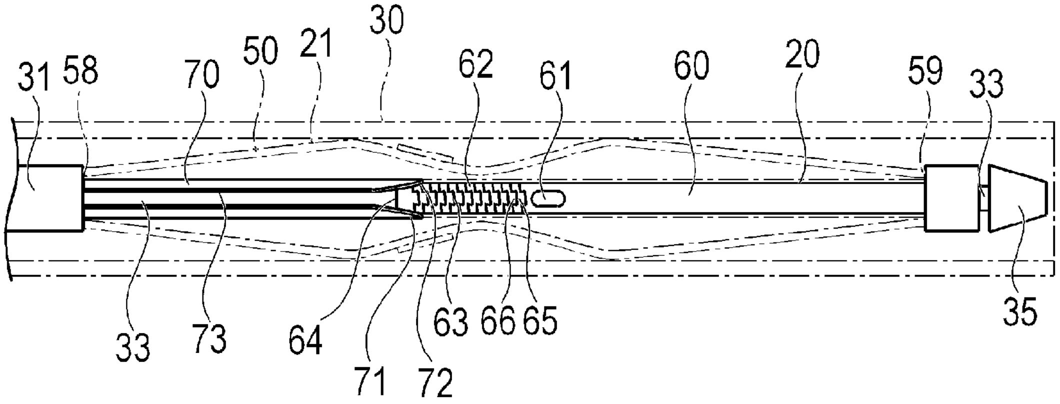
FIGS. 3(A)-3(C) illustrate front views of the vicinity of an outer tube and an inner tube through a storage sheath and through the expansion body.
Figure 3B:
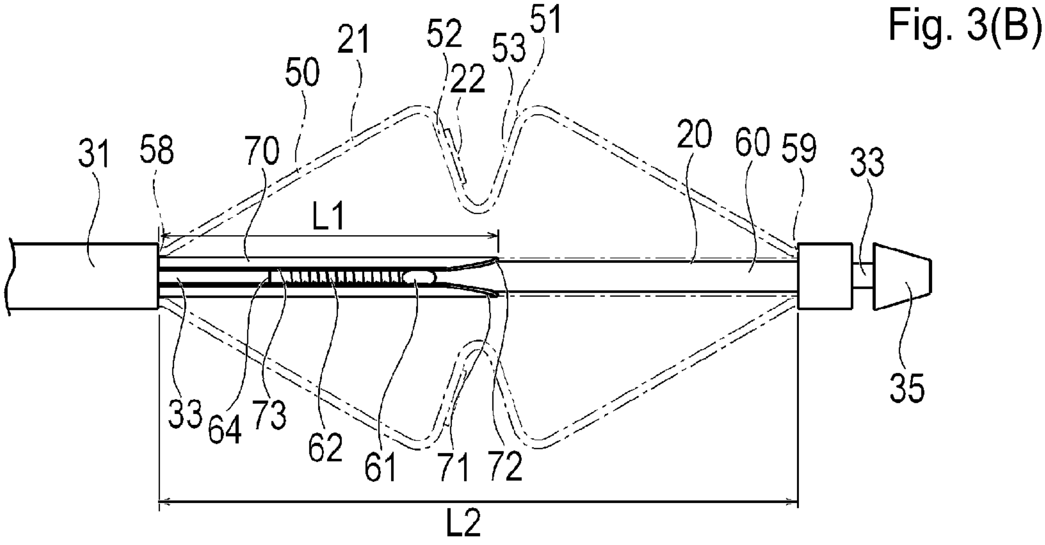

Next, the outer tube 70 and the inner tube 60 will be described. As illustrated in FIGS. 2 and 3(B), the outer tube 70 extends to the distal side from the first connecting portion 58 at the proximal portion of the expansion body 21. The outer tube 70 includes an opening end (open end) 72 at which an opening portion 71 is formed, on the distal side. In addition, a first engagement portion 73 having a slit shape and extending from the opening end 72 to the proximal side along the axial direction is formed in the outer tube 70. The first engagement portion 73 has such a width in the circumferential direction that a second engagement portion 61 formed in the inner tube 60 can enter the first engagement portion 73. It is preferable that the width of the first engagement portion 73 in the circumferential direction is widened at a distal portion of the first engagement portion 73. Accordingly, the first engagement portion 73 easily receives the second engagement portion 61 from the distal side. The outer tube 70 includes one first engagement portion 73, but may include two or more first engagement portions 73 at different locations in the circumferential direction. In a natural state where no external force acts on the expansion body 21, the expansion body 21 is in a reference form where the expansion body 21 is deployed in the radial direction. In the reference form, the opening end 72 is located closer to the distal side than the first connecting portion 58, and is closer to the proximal side than the second connecting portion 59.

In the reference form where the expansion body 21 is widened with no external force acting on the expansion body 21, a distance L1 from the first connecting portion 58 to the opening end 72 is more than 0% of a distance L2 from the first connecting portion 58 to the second connecting portion 59, preferably 30% to 80%, more preferably 40% to 70%, and further preferably 50% to 60%. When the distance L1 is too short, the range where the outer tube 70 and the inner tube 60 overlap each other between the first connecting portion 58 and the second connecting portion 59 is shortened, so that the effect of making the shaft portion difficult to bend in the reference form is decreased. When the distance L1 is too long, the range where the outer tube 70 and the inner tube 60 overlap each other between the first connecting portion 58 and the second connecting portion 59 is lengthened, so that the effect of making the shaft portion 20 easy to bend in a contracted form where the expansion body 21 is contracted (refer to FIG. 3(A)) is decreased.

Figure 3C:
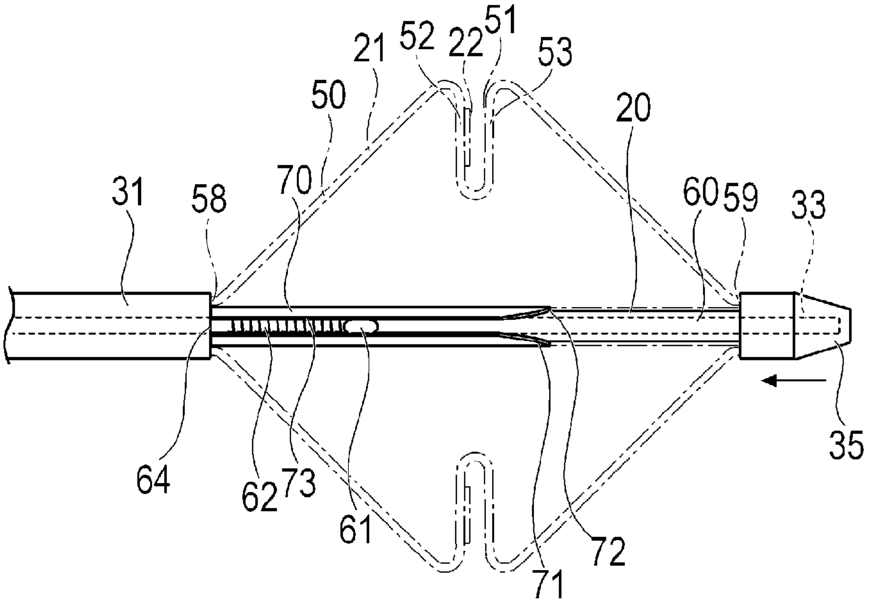

The inner tube 60 is slidable in the axial direction inside the outer tube 70. The inner tube 60 extends to the proximal side or in the proximal direction from the second connecting portion 59 at the distal portion of the expansion body 21. A proximal-most end 64 of the inner tube 60 is located closer to the proximal side than the opening end 72 of the outer tube 70. That is, the proximal-most end 64 of the inner tube 60 is proximal of the opening end 72 of the outer tube 70. The inner tube 60 includes a flexible portion 62 that has lower flexural rigidity and is easier to bend than a portion of the inner tube 60 adjacent to the flexible portion 62 in the axial direction. The flexible portion 62 can be disposed inside the outer tube 70 as illustrated in FIGS. 3(B) and 3(C), and can be extracted from the outer tube 70 to the distal side and disposed closer to the distal side than the outer tube 70 as illustrated in FIG. 3(A). The flexible portion 62 is formed in a spiral shape by forming a slit portion 63 having a spiral shape and penetrating through the flexible portion 62 from an outer peripheral surface to an inner peripheral surface. The slit portion 63 can be easily formed by, for example, laser processing. Protruding portions 66 to be fitted to a recessed portion 65 and to a recessed portion 65 are formed in surfaces that face each other while interposing the slit portion 63 therebetween. The protruding portions 66 are widened on a protruding direction side. For this reason, the protruding portion 66 has a structure where the protruding portion 66 does not come off from the recessed portion 65. Therefore, the flexible portion 62 has a structure where the flexible portion 62 is easy to bend but is strong against a tensile force. In addition, the second engagement portion 61 protruding outward in the radial direction is formed on an outer peripheral surface of the inner tube 60. As illustrated in FIGS. 3(B) and 3(C), the second engagement portion 61 can slidably enter the first engagement portion 73 of the outer tube 70. The second engagement portion 61 is formed closer to the distal side than the flexible portion 62 (i.e., the second engagement portion 61 is distal of the flexible portion 62), but the position of the second engagement portion 61 is not particularly limited. Therefore, the second engagement portion 61 may be formed closer to the proximal side than the flexible portion 62, or may be formed to overlap the flexible portion 62.

It is preferable that the storage sheath 30 and the main shaft 31 of the shaft portion 20 are made of a material having a certain degree of flexibility. Examples of such a material include polyolefins such as polyethylene, polypropylene, polybutene, ethylene-propylene copolymer, ethylene-vinyl acetate copolymer, ionomer, and a mixture of two or more thereof, fluororesins such as soft polyvinyl chloride resin, polyamide, polyamide elastomer, polyether blockamide, polyester, polyester elastomer, polyurethane, and polytetrafluoroethylene, polyimide, PEEK, silicone rubber, and latex rubber.

The pulling shaft 33 can be made of, for example, an elongate wire such as a metallic material such as stainless steel or a super-elastic alloy such as a nickel-titanium alloy or a copper-zinc alloy, or a resin material having relatively high rigidity. In addition, the pulling shaft 33 may be formed by coating the above material with a resin material such as polyvinyl chloride, polyethylene, polypropylene, ethylene-propylene copolymer, or fluororesin.

The distal member 35, the inner tube 60, and the outer tube 70 can be made of, for example, a metallic material such as stainless steel or a super-elastic alloy such as a nickel-titanium alloy or a copper-zinc alloy, or a resin material having relatively high rigidity.

Next, a treatment method using the medical device 10 according to the present embodiment will be described. The treatment method is performed on a patient suffering from a heart failure (left heart failure). More specifically, as illustrated in FIG. 4, the treatment method is performed on a patient suffering from a chronic heart failure in which a myocardium of a left ventricle of the heart H is hypertrophied and increases in stiffness (hardness) to cause an increase in blood pressure in a left atrium HLa.

When the operator forms the through-hole Hh, the operator delivers an introducer in which a guiding sheath and a dilator are combined together, to the vicinity of the atrial septum HA. The introducer can be delivered to, for example, a right atrium HRa via an inferior vena cava Iv. In addition, the introducer can be delivered using the guide wire 11. The operator can insert the guide wire 11 into the dilator, and deliver the introducer along the guide wire 11. The insertion of the introducer into or the insertion of the guide wire 11 into a living body can be performed using a known method such as using an introducer for blood vessel introduction.

Next, the operator causes a puncture device and the dilator to penetrate through the atrial septum HA from a right atrium HRa side toward a left atrium HLa side to form the through-hole Hh. For example, a device such as a wire having a sharp distal end can be used as the puncture device. The puncture device is inserted into the dilator, and is delivered to the atrial septum HA. After the guide wire 11 is removed from the dilator, instead of the guide wire 11, the puncture device can be delivered to the atrial septum HA.

Figure 5:
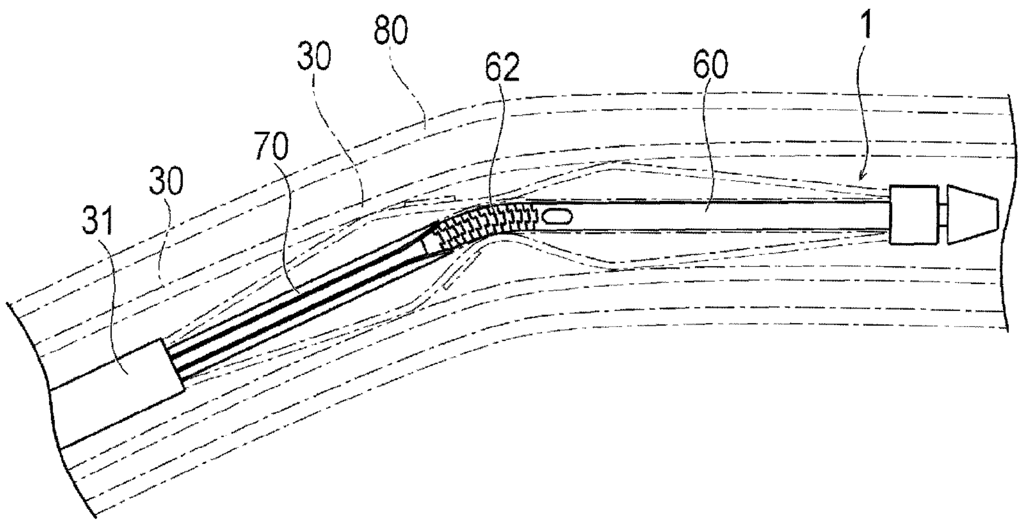
FIG. 5 is a front view illustrating the medical device that is bent in a delivery sheath, through the storage sheath and through the expansion body.

Next, the operator delivers the medical device 10 to the vicinity of the atrial septum HA along the guide wire 11 inserted into the left atrium HLa from the right atrium HRa via the through-hole Hh in advance. At this time, a part of a distal portion of the medical device 10 passes through the through-hole Hh opened in the atrial septum HA, and reaches the left atrium HLa. In addition, when the medical device 10 is inserted, as illustrated in FIG. 3(A), the expansion body 21 is in the contracted form where the expansion body 21 is stored in the storage sheath 30. In the contracted form, the proximal side outward projection portion 55, the inward projection portion 56, and the distal side outward projection portion 57 that have a projection shape in the reference form are elastically deformed into a shape close to being flat, so that the expansion body 21 is contracted in the radial direction. In the contracted form, the flexible portion 62 of the inner tube 60 is located closer to the distal side than the outer tube 70 (i.e., the flexible portion 62 is distal of the outer tube 70). For this reason, the flexible portion 62 is not covered with the outer tube 70. Accordingly, the flexible portion 62 can be flexibly bent. Therefore, as illustrated in FIG. 5, when the flexible portion 62 is moved in a delivery sheath 80 for transporting the distal portion of the medical device 10 to a target position in the living body, or in a blood vessel, the flexible portion 62 can be easily bent according to the bending of the delivery sheath 80 or of the blood vessel. For this reason, the passability of the medical device 10 in the delivery sheath 80 or in the blood vessel is improved.

Figure 6:
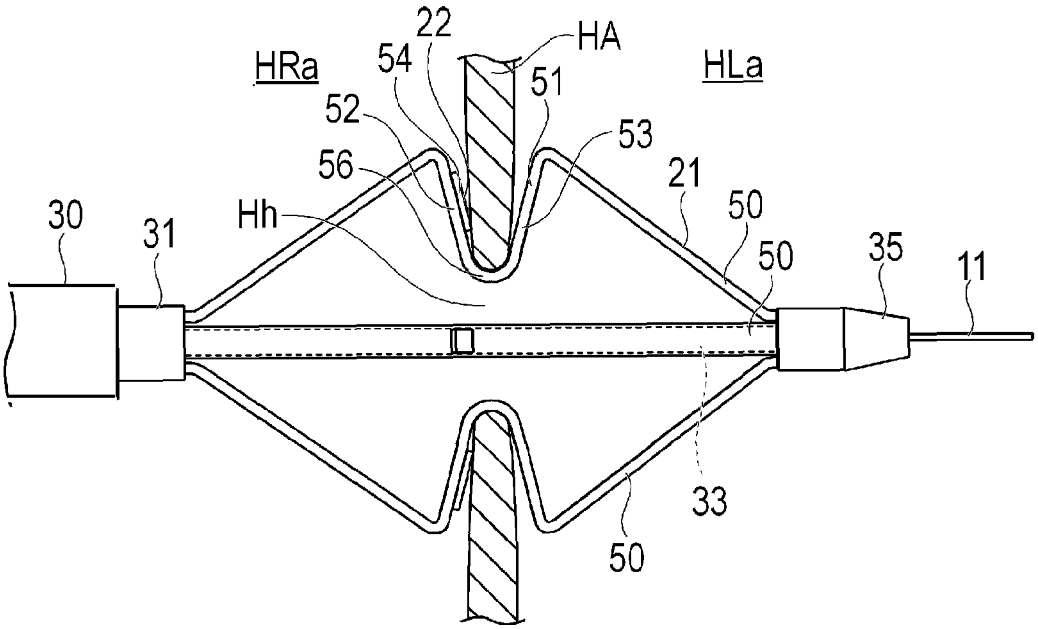
FIG. 6 is a view for schematically describing a state where the expansion body is disposed in the atrial septum, in which the medical device and the biological tissue are illustrated in a front view and in a cross-sectional view, respectively.

Next, the storage sheath 30 is moved to the proximal side or in the proximal direction to expose a distal side portion of the expansion body 21 into the left atrium HLa. Accordingly, the distal side portion of the expansion body 21 is deployed in the radial direction inside the left atrium HLa by its own restoring force. Next, as illustrated in FIGS. 3(B) and 6, the storage sheath 30 is moved to the proximal side to expose the entirety of the expansion body 21. Accordingly, a proximal side portion of the expansion body 21 is deployed in the radial direction inside the right atrium HRa by its own restoring force. At this time, the inward projection portion 56 is disposed inside the through-hole Hh. Accordingly, the entirety of the expansion body 21 is deployed by its own elastic force, and restores to the original reference form or to a form close to the reference form. At this time, the atrial septum HA is disposed between the proximal side holding portion 52 and the distal side holding portion 53. The expansion body 21 may come into contact with the through-hole Hh, thereby returning to a shape close to the reference form instead of completely returning to the reference form. In this state, the expansion body 21 is not covered with the storage sheath 30 and does not receive a force from the pulling shaft 33. This form of the expansion body 21 can be defined as being included in the reference form.

When the expansion body 21 is deformed from the contracted state into the reference form, the first connecting portion 58 and the second connecting portion 59 approach each other. Accordingly, the inner tube 60 connected to the second connecting portion 59 moves to the proximal side or in the proximal direction. For this reason, the flexible portion 62 of the inner tube 60 enters the inside of the outer tube 70 from the opening portion 71. For this reason, the flexible portion 62 is surrounded by the outer tube 70, and overlaps the outer tube 70. As a result, the flexible portion 62 is difficult to bend. In addition, the range in the axial direction where the outer tube 70 and the inner tube 60 overlap each other is longer in the reference form (refer to FIG. 3(B)) and in an expanded form (refer to FIG. 3(C)) than in the contracted form (refer to FIG. 3(A)). For this reason, the outer tube 70 and the inner tube 60 between the first connecting portion 58 and the second connecting portion 59 are more difficult to bend in the reference form and in the expanded form than in the contracted form. For this reason, the expansion body 21 can be uniformly widened to cause an expansion force to uniformly act on the through-hole Hh of the atrial septum HA.

In addition, when the expansion body 21 is in the reference form, the second engagement portion 61 protruding from the outer peripheral surface of the inner tube 60 is accommodated in the first engagement portion 73 having a slit shape which is formed in the outer tube 70. Accordingly, the first engagement portion 73 and the second engagement portion 61 engage with each other, and the inner tube 60 is not rotatable with respect to the outer tube 70. For this reason, it is possible to suppress the twisting of the expansion body 21. For this reason, the expansion body 21 can be uniformly widened with a uniform expansion force to cause an expansion force to uniformly act on the through-hole Hh of the atrial septum HA.

Figure 7:
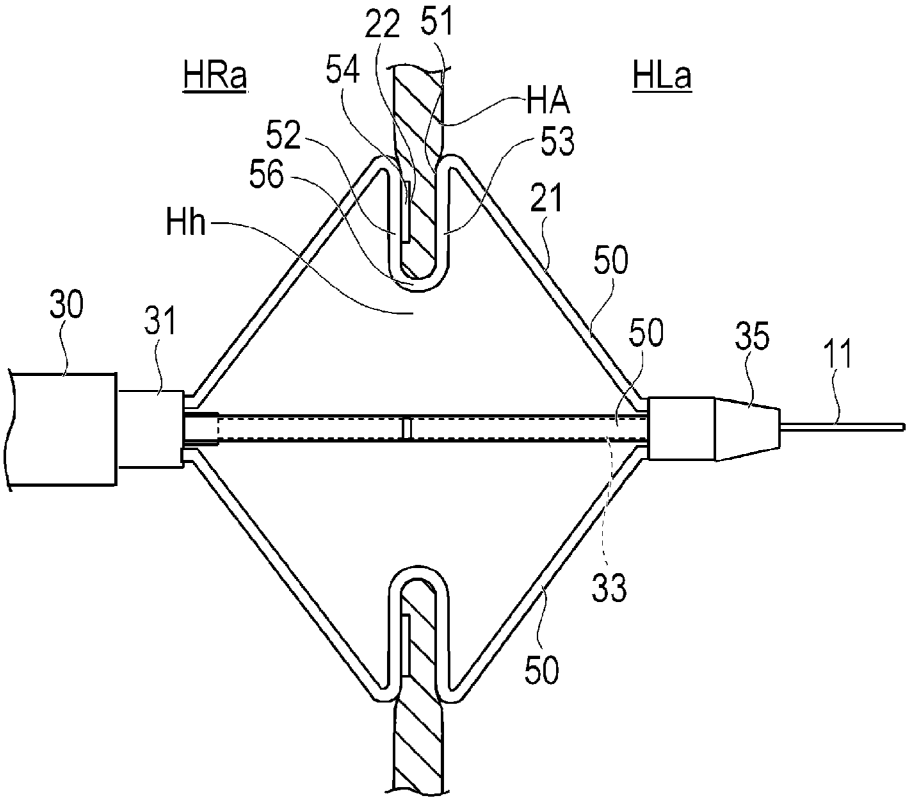
FIG. 7 is a view for schematically describing a state where the expansion body is expanded in diameter in the atrial septum, in which the medical device and the biological tissue are illustrated in a front view and in a cross-sectional view, respectively.

Next, the operator operates the operation unit 23 in a state where the atrial septum HA is held by the holding portion 51, to move the pulling shaft 33 to the proximal side. Accordingly, as illustrated in FIGS. 3(C) and 7, the expansion body 21 receiving a compression force in the axial direction is deformed into the expanded form where the expansion body 21 is more expanded in the radial direction than in the reference form. In the expanded form of the expansion body 21, the proximal side holding portion 52 and the distal side holding portion 53 approach each other, and the atrial septum HA is held between the proximal side holding portion 52 and the distal side holding portion 53. The holding portion 51 additionally expands in a state where the holding portion 51 holds the atrial septum HA, to widen the through-hole Hh in the radial direction.

In the expanded form, similarly to the reference form, the flexible portion 62 is surrounded by the outer tube 70, and axially overlaps the outer tube 70. For this reason, the flexible portion 62 is difficult to bend. In addition, since the range in the axial direction where the outer tube 70 and the inner tube 60 axially overlap each other is longer in the expanded form than in the contracted form, the outer tube 70 and the inner tube 60 between the first connecting portion 58 and the second connecting portion 59 are difficult to bend in the expanded form. For this reason, even when the outer tube 70 and the inner tube 60 between the first connecting portion 58 and the second connecting portion 59 receives a compression force due to pulling of the pulling shaft 33, the outer tube 70 and the inner tube 60 are difficult to buckle. Therefore, the expansion body 21 can be uniformly widened with a uniform expansion force to uniformly widen the through-hole Hh in the radial direction.

In addition, in the expanded form, similarly to the reference form, the first engagement portion 73 and the second engagement portion 61 engage with each other, and the inner tube 60 is not rotatable with respect to the outer tube 70. For this reason, it is possible to suppress the twisting of the expansion body 21. For this reason, the expansion body 21 can be uniformly widened with a uniform expansion force to uniformly widen the through-hole Hh in the radial direction.

Figure 12:
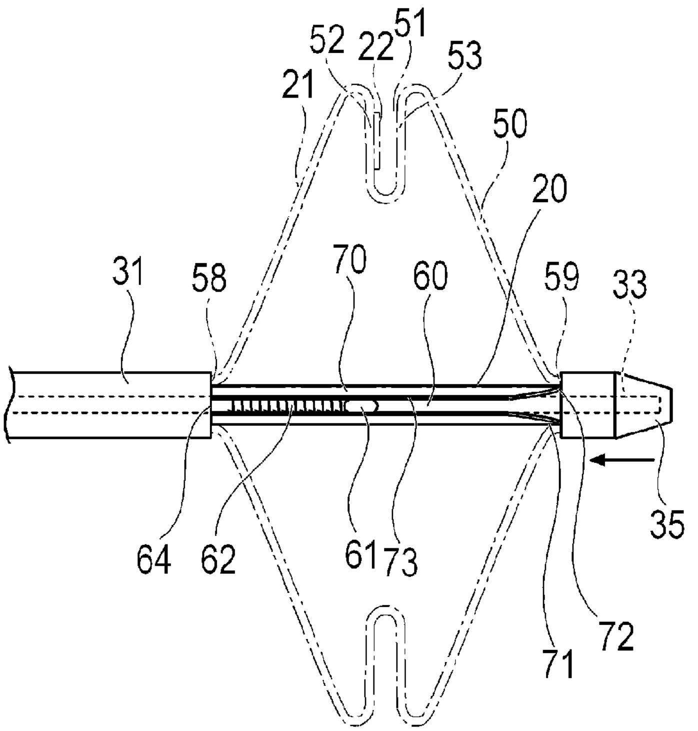
FIG. 12 is a front view of an expanded form illustrating the vicinity of the outer tube and the inner tube through the storage sheath and through the expansion body.

In the expanded form, when the operator moves the pulling shaft 33 further to the proximal side than in the state illustrated in FIGS. 3(C) and 7, as illustrated in FIG. 12, the opening end 72 that is a distal side end portion of the outer tube 70 abuts against the second connecting portion 59. Accordingly, a relative axial movement between the outer tube 70 and the inner tube 60 is limited, and excessive expansion of the expansion body 21 is limited. As a result, excessive expansion of the through-hole Hh can be limited, and safety can be improved. The proximal-most end 64 of the inner tube 60 may abut against, for example, a structure protruding from an inner peripheral surface of the outer tube 70 before the opening end 72 of the outer tube 70 abuts against the second connecting portion 59 when the operator moves the pulling shaft 33 to the proximal side. Even with such a configuration, a relative movement between the outer tube 70 and the inner tube 60 can be limited, and excessive expansion of the expansion body 21 can be limited. As a result, excessive expansion of the through-hole Hh can be limited, and safety can be improved.

After the through-hole Hh is expanded, hemodynamics is confirmed. As illustrated in FIG. 4, the operator delivers a hemodynamics confirmation device 100 to the right atrium HRa via the inferior vena cava Iv. For example, a known echo catheter can be used as the hemodynamics confirmation device 100. The operator can cause a display device such as a display to display an echo image acquired by the hemodynamics confirmation device 100, and confirm the amount of blood passing through the through-hole Hh, based on a display result.

Next, the operator performs a maintenance treatment to maintain the size of the through-hole Hh. In the maintenance treatment, energy is applied to an edge portion of the through-hole Hh through the energy transmission element 22, so that the edge portion of the through-hole Hh is cauterized (heated and cauterized) by the energy. When a biological tissue in the vicinity of the edge portion of the through-hole Hh is cauterized through the energy transmission element 22, a degenerated portion in which the biological tissue is degenerated is formed in the vicinity of the edge portion. Since the biological tissue in the degenerated portion is in a state where elasticity is lost, the through-hole Hh can maintain a shape when the through-hole Hh is widened by the expansion body 21.

In the expanded form, as described above, since the expansion body 21 is uniformly widened with a uniform expansion force, the energy transmission element 22 provided in each of the wire portions 50 is properly pressed against the atrial septum HA. In addition, the energy transmission element 22 is disposed on the projection portion 54 of the proximal side holding portion 52. For this reason, the maintenance treatment is performed in a state where the energy transmission element 22 is buried in the biological tissue by pressing the projection portion 54 against the atrial septum HA. Accordingly, the energy transmission element 22 does not come into contact with the blood during the maintenance treatment, so that it is possible to suppress the generation of blood clots or the like caused by the leakage of a current to the blood.

After the maintenance treatment, hemodynamics is confirmed again, and when the amount of the blood passing through the through-hole Hh reaches a desired amount, the operator reduces the expansion body 21 in diameter. The operator moves the storage sheath 30 with respect to the expansion body 21 in a distal end direction. Accordingly, the expansion body 21 is stored in the storage sheath 30 from the proximal side, and is in the contracted form. Further, the operator removes the entirety of the medical device 10 out of the living body to end the treatment.

As described above, the medical device 10 according to the aforementioned embodiment is a medical device including: the shaft portion 20 that is elongate; and the expansion body 21 provided at the distal portion of the shaft portion 20 to be expandable and contractable in a radial direction. The shaft portion 20 includes the outer tube 70, and the inner tube 60 that is slidable in the axial direction inside the outer tube 70. The expansion body 21 includes the first connecting portion 58 connected to the outer tube 70, and the second connecting portion 59 connected to the inner tube 60. The outer tube 70 includes the opening end 72 at which the opening portion 71 is formed, the inner tube 60 entering and exiting from the opening portion 71. The expansion body 21 is settable to or positionable in the reference form where the expansion body 21 is widened in the radial direction in a natural state, and is settable to or positionable in the contracted form where the expansion body 21 is contracted in the radial direction, when the first connecting portion 58 and the second connecting portion 59 are more separated from each other compared to the reference form. In the reference form, the opening end 72 is located between the first connecting portion 58 and the second connecting portion 59, and when the expansion body 21 is deformed from the reference form into the contracted form, a part of the inner tube 60 is extracted from the opening portion 71. Accordingly, in the medical device 10, in the contracted form where the inner tube 60 is extracted from the outer tube 70, the range where the outer tube 70 and the inner tube 60 overlap (axially overlap) each other between the first connecting portion 58 and the second connecting portion 59 is shortened. For this reason, in the contracted form where the expansion body 21 is contracted, the flexibility of the medical device 10 between the first connecting portion 58 and the second connecting portion 59 is improved, and the passability of the medical device 10 in a tubular member such as the delivery sheath 80 or in a biological lumen is improved. In addition, in the medical device 10, in the reference form where the expansion body 21 is expanded, the range where the outer tube 70 and the inner tube 60 overlap each other between the first connecting portion 58 and the second connecting portion 59 is lengthened. For this reason, in the medical device 10, the shaft portion 20 is difficult to bend between the first connecting portion 58 and the second connecting portion 59. For this reason, the medical device 10 can maintain the expansion body 21 in a proper shape in the reference form, so that a decrease in expansion force can be suppressed and a biological tissue can be uniformly widened in the radial direction. The first connecting portion 58 of the expansion body 21 may be directly connected to the outer tube 70 or may be indirectly connected to the outer tube 70 via another member. In addition, the second connecting portion 59 of the expansion body 21 may be directly connected to the inner tube 60 or may be indirectly connected to the inner tube 60 via another member.

In addition, the expansion body 21 is settable to or positionable in the expanded form where the expansion body 21 is expanded in the radial direction, when the first connecting portion 58 and the second connecting portion 59 approach each other from the reference form, and when the expansion body 21 is deformed from the reference form into the expanded form, a part of the inner tube 60 is stored inside or positioned in the outer tube 70 from the opening portion 71. Accordingly, even when a compression force is acted on the expansion body 21 in the axial direction to set the expansion body 21 to the expanded form where the expansion body 21 is more expanded in the radial direction than in the reference form, the shaft portion 20 is difficult to bend between the first connecting portion 58 and the second connecting portion 59, so that buckling can be suppressed. For this reason, in the medical device 10, the expansion body 21 is settable to the expanded form of a desired shape that is uniform in the circumferential direction, so that a decrease in expansion force can be suppressed and a biological tissue can be uniformly widened in the radial direction.

In addition, the inner tube 60 includes the flexible portion 62 having lower flexural rigidity than a portion adjacent to the flexible portion 62 in the axial direction. In the reference form, the flexible portion 62 is located in a range where the outer tube 70 and the inner tube 60 overlap (axially overlap) each other. In the contracted form, the flexible portion 62 is located in a range different from the range where the outer tube 70 and the inner tube 60 axially overlap each other. Accordingly, in the contracted form, the flexible portion 62 is located outside the range where the outer tube 70 and the inner tube 60 overlap each other, so that the flexible portion 62 can be flexibly bent. For this reason, in the contracted form, the flexibility of the medical device 10 between the first connecting portion 58 and the second connecting portion 59 is improved, and the passability of the medical device 10 in a tubular member such as the delivery sheath 80 or in a biological lumen is improved. In addition, in the reference form, since the flexible portion 62 is located in the range where the outer tube 70 and the inner tube 60 overlap each other, the medical device 10 is difficult to bend between the first connecting portion 58 and the second connecting portion 59. Therefore, the medical device 10 can maintain the expansion body 21 in a proper shape in the reference form, so that a decrease in expansion force can be suppressed and a biological tissue can be uniformly widened in the radial direction.

In addition, the outer tube 70 includes the first engagement portion 73. The inner tube 60 includes the second engagement portion 61. At least in the reference form, the first engagement portion 73 and the second engagement portion 61 are slidable in the axial direction, and come into contact with each other in the circumferential direction to limit relative rotation between the outer tube 70 and the inner tube 60. Accordingly, at least in the reference form, relative rotation between the outer tube 70 and the inner tube 60 is limited. For this reason, at least in the reference form, the twisting of the expansion body 21 can be suppressed. Therefore, in the medical device 10, the expansion body 21 is settable to the reference form of a desired shape, and a decrease in expansion force can be suppressed.

In addition, the flexible portion 62 is formed of the slit portion 63 having a spiral shape provided in the inner tube 60. Accordingly, the flexible portion 62 can be flexibly bent and easily processed.

Another aspect of the disclosure here involves the treatment method. The treatment method is a treatment method in which the through-hole Hh that is opened in a biological tissue is widened using the medical device 10, in which the medical device 10 includes the shaft portion 20 that is elongate, and the expansion body 21 provided at the distal portion of the shaft portion 20 to be expandable and contractable in the radial direction, the shaft portion 20 includes the outer tube 70, and the inner tube 60 that is slidable in the axial direction inside the outer tube 70, the expansion body 21 includes the first connecting portion 58 connected to the outer tube 70, and the second connecting portion 59 connected to the inner tube 60, the outer tube 70 includes the opening end 72 at which the opening portion 71 is formed, the inner tube 60 entering and exiting from the opening portion 71, and the expansion body 21 is settable to the reference form where the expansion body 21 is widened in the radial direction, and is settable to the contracted form where the expansion body 21 is contracted in the radial direction, when the first connecting portion 58 and the second connecting portion 59 are more separated from each other than in the reference form, the method including: transporting the expansion body 21 in a living body and inserting the expansion body 21 into the through-hole Hh that is opened in the biological tissue, with the expansion body 21 set to the contracted form; and widening the through-hole Hh using the expansion body 21 with the expansion body 21 set to the reference form inside the through-hole Hh.

In the treatment method configured as described above, in the contracted form where the inner tube 60 is extracted from the outer tube 70, the range where the outer tube 70 and the inner tube 60 overlap each other between the first connecting portion 58 and the second connecting portion 59 is shortened. For this reason, according to the treatment method, in the contracted form where the expansion body 21 is contracted, flexibility between the first connecting portion 58 and the second connecting portion 59 is improved, and passability in a tubular member such as the delivery sheath 80 or in a biological lumen is improved. In addition, in the reference form where the expansion body 21 is expanded, the range where the outer tube 70 and the inner tube 60 overlap each other between the first connecting portion 58 and the second connecting portion 59 is lengthened. For this reason, in the medical device 10, the shaft portion 20 is difficult to bend between the first connecting portion 58 and the second connecting portion 59. For this reason, according to the treatment method, the expansion body 21 can be maintained in a proper shape in the reference form, so that a decrease in expansion force can be suppressed and a biological tissue can be uniformly widened in the radial direction.

The invention is not limited only to the aforementioned embodiment and various modifications can be made by those skilled in the art without departing from the technical concept of the invention. For example, the biological lumen to which the medical device 10 is applied is not limited to blood vessels, and may be, for example, a vessel, a ureter, a bile duct, an ovarian duct, a hepatic duct, a lymph duct, or the like.

Figure 8A:
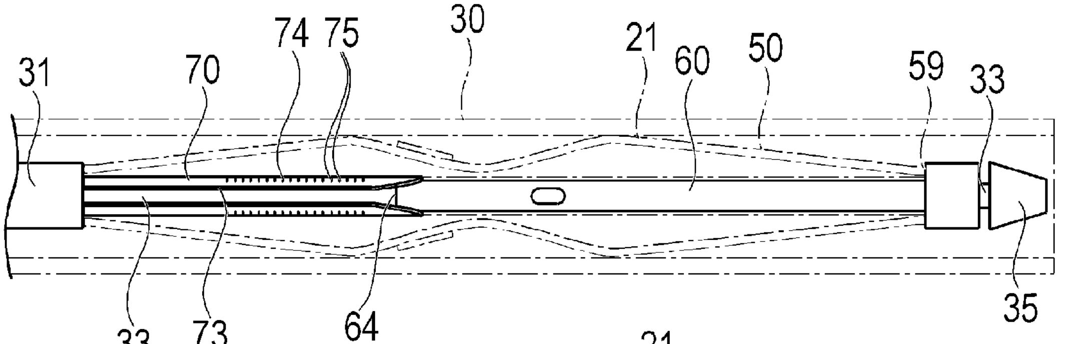
FIGS. 8(A) and 8(B) illustrate plan views of the vicinity of an outer tube and an inner tube of a medical device according to a first modification example through a storage sheath and through an expansion body.
Figure 8B:
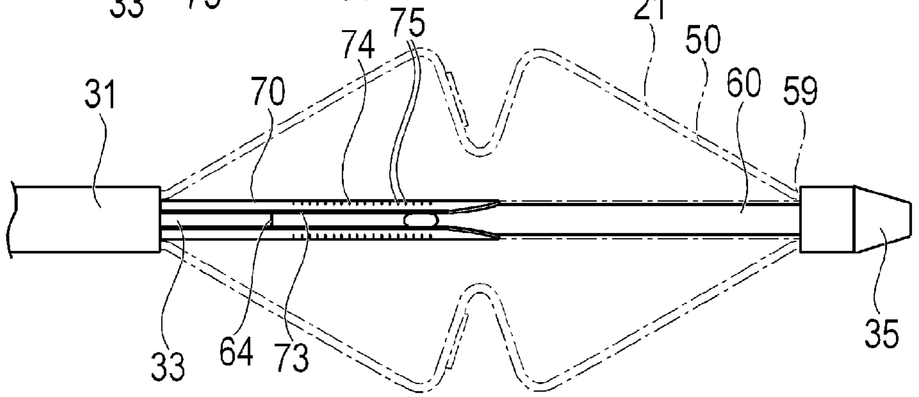

In addition, as in a first modification example illustrated in FIGS. 8(A) and 8(B), a flexible portion 74 may be formed not in the inner tube 60 but in the outer tube 70. The flexible portion 74 is formed of, for example, a plurality of slit portions 75. In the contracted form, as illustrated in FIG. 8(A), the flexible portion 74 of the outer tube 70 is disposed at a position where the flexible portion 74 does not overlap (axially overlap) the inner tube 60 in the axial direction. For this reason, the flexible portion 74 of the outer tube 70 can be easily bent. In addition, in the reference form and in the expanded form, as illustrated in FIG. 8(B), the flexible portion 74 of the outer tube 70 is disposed at a position where the flexible portion 74 overlaps the inner tube 60 in the axial direction. For this reason, the flexible portion 74 of the outer tube 70 is difficult to bend. In addition, the medical device 10 may include both the inner tube 60 including the flexible portion 74 illustrated in FIG. 3, and the outer tube 70 including the flexible portion 74 illustrated in FIGS. 8(A) and 8(B).

In addition, both the inner tube 60 and the outer tube 70 may not include the flexible portion 62. The range in the axial direction where the outer tube 70 and the inner tube 60 overlap each other is longer in the reference form (refer to FIG. 3(B)) and in the expanded form (refer to FIG. 3(C)) than in the contracted form (refer to FIG. 3(A)). For this reason, even when the outer tube 70 and the inner tube 60 between the first connecting portion 58 and the second connecting portion 59 do not include the flexible portion 62, bending is more difficult in the reference form and in the expanded form than in the contracted form.

Figure 9A:
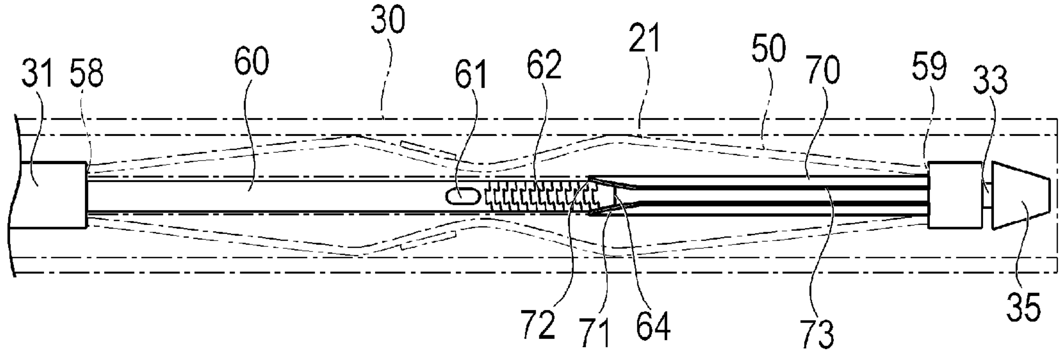
FIGS. 9(A) and 9(B) illustrate plan views of the vicinity of an outer tube and an inner tube of a medical device according to a second modification example through a storage sheath and through an expansion body.
Figure 9B:
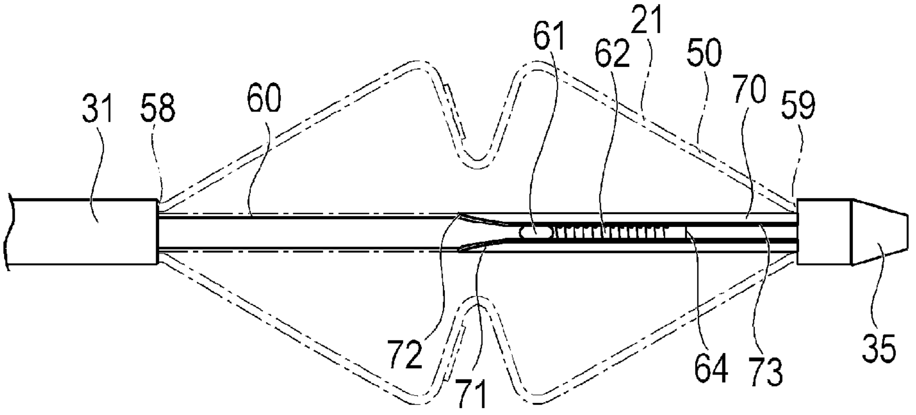

In addition, as in a second modification example illustrated in FIGS. 9(A) and 9(B), the outer tube 70 may be connected to the second connecting portion 59, and the inner tube 60 may be connected to the first connecting portion 58.

In addition, as in a third modification example illustrated in FIGS. 10(A) and 10(B), the medical device 10 may not include the expansion body 21. The distal portion of the pulling shaft 33 is connected to the inner tube 60. When an operator pulls the pulling shaft 33, as illustrated in FIG. 10(B), the medical device 10 is set to the accommodated form where at least a part of the inner tube 60 including the flexible portion 62 is disposed at a position where at least the part overlaps (axially overlaps) the outer tube 70. In addition, when the operator pushes the pulling shaft 33, as illustrated in FIG. 10(A), the medical device 10 is set to the extended form where the flexible portion 62 of the inner tube 60 is disposed at a position where the flexible portion 62 does not overlap the outer tube 70.

As described above, the medical device 10 according to the third modification example includes the shaft portion 20 that is elongate. The shaft portion 20 includes the outer tube 70, and the inner tube 60 that is slidable in the axial direction inside the outer tube 70. The outer tube 70 includes the opening end 72 at which the opening portion 71 is formed, the inner tube 60 entering and exiting from the opening portion 71. The shaft portion 20 is settable to the accommodated form where at least a part of the inner tube 60 is accommodated in the outer tube 70, and is settable to the extended form where the inner tube 60 is extracted from the opening portion 71 from the accommodated form. The outer tube 70 and/or the inner tube 60 includes the flexible portion 62 having lower flexural rigidity than a portion adjacent to the flexible portion 62 in the axial direction. In the accommodated form, the flexible portion 62 is located in a range where the outer tube 70 and the inner tube 60 overlap each other, and in the extended form, the flexible portion 62 is located in a range different from the range where the outer tube 70 and the inner tube 60 overlap each other. Accordingly, in the extended form, the flexible portion 62 is located outside the range where the outer tube 70 and the inner tube 60 overlap each other, so that the flexible portion 62 can be flexibly bent. For this reason, in the extended form, the flexibility of the medical device 10 between the first connecting portion 58 and the second connecting portion 59 is improved, and the passability of the medical device 10 in a tubular member such as the delivery sheath 80 or in a biological lumen is improved. In addition, in the accommodated form, the flexible portion 62 is located in the range where the outer tube 70 and the inner tube 60 overlap each other. For this reason, in the accommodated form, it is possible to make the medical device 10 difficult to bend between the first connecting portion 58 and the second connecting portion 59. The medical device 10 can be, for example, a catheter that bends easily until the catheter reaches a stenosed site and is difficult to bend at the stenosed site to exert a strong pushing force, a catheter that forms a bent or meandering lumen into a linear shape, and the like.

In addition, the form of the flexible portion 62 is not particularly limited as long as the flexible portion 62 is more flexible than a portion adjacent to the flexible portion 62 in the axial direction. For example, the flexible portion 62 may be formed as a non-through groove in the inner peripheral surface and/or in the outer peripheral surface of the inner tube 60 or the outer tube 70. In addition, as illustrated in FIG. 11(A), the flexible portion 62 may be a slit portion or a non-through groove that is formed to extend in the circumferential direction instead of having a spiral shape. In addition, as illustrated in FIG. 11(B), the flexible portion 62 may be a plurality of through-holes or a plurality of non-through holes. In addition, as illustrated in FIG. 11(C), the flexible portion 62 may be formed to be thinner than a portion adjacent to the flexible portion 62 in the axial direction. In addition, as illustrated in FIG. 11(D), the flexible portion 62 may be formed in a coil shape. In addition, as illustrated in FIG. 11(E), the flexible portion 62 may be formed by twisting or knitting a plurality of wires. In addition, the flexible portion 62 may be made of a material softer than the material of a portion adjacent to the flexible portion 62 in the axial direction. The hardness (softness) of the material can be specified by, for example, Rockwell hardness, Brinnel hardness, Vickers hardness, Shore hardness, durometer hardness, and the like.

In addition, the inner tube 60 may be connected to the second connecting portion 59 so as to be slightly movable. In addition, the outer tube 70 may be connected to the first connecting portion 58 so as to be slightly movable.

The detailed description above describes embodiments of a medical device and treatment method representing examples of the medical device and treatment method disclosed here. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

REFERENCE SIGNS LIST

10: Medical device
11: Guide wire
20: Shaft portion
21: Expansion body
30: Storage sheath
58: First connecting portion
59: Second connecting portion
60: Inner tube
61: Second engagement portion
62, 74: Flexible portion
63, 75: Slit portion
70: Outer tube
71: Opening portion
72: Opening end
73: First engagement portion
74: Flexible portion

What is claimed is:

1. A medical device comprising:

an elongate shaft portion that extends in an axial direction from a distal portion of the shaft portion to a proximal portion of the shaft portion;

an expansion body configured to be outwardly expanded in a radial direction and inwardly contracted in the radial direction, the expansion body being located at the distal portion of the shaft portion;

the shaft portion including an outer tube, and an inner tube that is slidable in an axial direction inside the outer tube;

the expansion body including a first connecting portion connected to the outer tube, the expansion body also including a second connecting portion connected to the inner tube so that sliding movement of the inner tube in the axial direction results in movement of the second connecting portion of the expansions body in the axial direction;

the outer tube including an open end, the inner tube entering the outer tube by way of the open end and exiting from the outer tube by way of the open end;

the expansion body being positionable in a reference form in which the expansion body is widened in the radial direction in a natural state with no external force acting on the expansion body, and being positionable in a contracted form in which the expansion body is contracted in the radial direction so that the expansion body in the contracted form is radially contracted relative to the expansion body in the reference form, the first connecting portion and the second connecting portion being more axially separated from each other in the contracted form than in the reference form;

the open end of the outer tube being located between the first connecting portion and the second connecting portion when the expansion body is in the reference form, and a part of the inner tube moving from inside the outer tube to outside the outer tube by passing through the open end; and a distance in the axial direction from the first connecting portion to the open end being a first axial distance, a distance in the axial direction from the first connecting portion to the second connecting portion being a second axial direction, the first axial distance being 30%-80% of the second axial distance in the natural state with no external force acting on the expansion body.

2. The medical device according to claim 1, wherein the expansion body is movable from the reference form to an expanded form in which the expansion body is outwardly expanded in the radial direction, the expansion body moving from the reference form to the expanded form when the first connecting portion and the second connecting portion approach each other, and when the expansion body moves from the reference form to the expanded form, a part of the inner tube moves from outside the outer tube to inside the outer through the open end.

3. The medical device according to claim 2, wherein the flexible portion is comprised of a slit portion or a groove having a spiral shape provided in the outer tube and/or in the inner tube.

4. The medical device according to claim 2, wherein the flexible portion is comprised of a plurality of wires.

5. The medical device according to claim 2, wherein the flexible portion is comprised of a coil-shaped flexible portion.

6. The medical device according to claim 2, wherein the flexible portion is made of a material softer than a material from which a portion adjacent to the flexible portion in the axial direction is made.

7. The medical device according to claim 2, wherein the open end is configured to abut against the second connecting portion of the expansion body when the expansion body is in the expanded form so as to limit an excessive expansion of the expansion body by limiting a relative movement between the outer tube and the inner tube.

8. The medical device according to claim 1, wherein the outer tube and/or the inner tube includes a flexible portion having lower flexural rigidity than a portion axially adjacent to the flexible portion, in the reference form, the flexible portion is located in a first range in which the outer tube and the inner tube axially overlap each other, and in the contracted form, the flexible portion is located in a second range different from the first range.

9. The medical device according to claim 1, wherein the outer tube includes a first engagement portion, the inner tube includes a second engagement portion, and at least in the reference form of the expansion body, the first engagement portion and the second engagement portion are slidable in the axial direction and are in contact with each other in a circumferential direction to limit relative rotation between the outer tube and the inner tube.

10. The medical device according to claim 1, wherein the elongate shaft portion includes a main shaft having a distal portion that terminates at a distal-most end of the main shaft, the outer tube being connected to the distal portion of the main shaft so that movement of the main shaft in the axial direction results in movement of the outer tube in the axial direction, the expansion body including a proximal end at which is located the first connecting portion that is connected to the outer tube, the proximal end of the expansion body being connected to the distal portion of the main shaft, the expansion body extending in a distal direction away from a distal-most end of the main shaft that faces in the axial direction, the outer tube extending in the distal direction away from the distal-most end surface of the main shaft.

11. The medical device according to claim 1, wherein the expansion body includes a proximal end at which is located the first connecting portion that is connected to the outer tube, the expansion body including a portion extending in a distal direction away from the proximal end of the expansion body and toward the second connection portion, the portion of the expansion body being a radially outwardly expanding portion that expands radially outwardly away from the outer tube when no external force is applied to the expansion body and that axially overlaps the outer tube so that a plane perpendicular to the outer tube and intersecting the outer tube also intersects the radially outwardly expanding portion of the expansion body.

12. The medical device according to claim 1, wherein the expansion body changes from the reference form to the contracted form by axial sliding movement of the inner tube in the axial direction relative to the outer tube in a direction away from the first connecting portion, the expansion body including a most-proximal portion extending in a distal direction from the first connecting portion toward the second connecting portion, the most-proximal portion of the expansion body contracting in the radial direction during the axial sliding movement of the inner tube relative to the outer tube in the distal direction away from the first connecting portion.

13. A medical device comprising:

an elongate shaft portion;

the shaft portion including an outer tube, and an inner tube that is slidable in an axial direction inside the outer tube;

the outer tube including an open end, the inner tube entering the outer tube and exiting the outer tube by way of the open end;

the shaft portion being positionable in an accommodated form in which at least a part of the inner tube is accommodated inside the outer tube, and being positionable in an extended form in which the at least a part of the inner tube is moved from inside the outer tube to outside the outer tube by way of the open end;

the outer tube and/or the inner tube including a flexible portion having lower flexural rigidity than a portion immediately axially adjacent to the flexible portion;

the flexible portion being located in a first range in which the outer tube and the inner tube axially overlap each other when the shaft portion is in the accommodated form; and the flexible portion being located in a second range in which the outer tube and the inner tube do not axially overlap each other when the shaft portion is in the extended form.

14. The medical device according to claim 13, wherein one end of the inner tube is a connected end that is connected to a connecting element and an opposite end of the inner tube is a free end, the flexible portion being provided on the inner tube, being spaced from the connected end of the inner tube, and being located closer to the free end of the inner tube than the connected end of the inner tube.

15. The medical device according to claim 13, wherein one end of the outer tube is a connected end that is connected to a connecting element and an opposite end of the outer tube is a free end, the flexible portion being provided on the outer tube, being spaced from the connected end of the outer tube, and being located closer to the free end of the outer tube than the connected end of the outer tube.

16. The medical device according to claim 13, wherein the inner tube includes a first engagement portion and the outer tube includes a second engagement portion, the first and second engagement portions engaging one another to limit relative rotation between the inner tube and the outer tube when the shaft portion is in the accommodated form, the first and second engagement portions being axially movable when the shaft portion is moved from the accommodated form to the extended form and being dis-engaged from one another when the shaft portion is in the extended form.

17. The medical device according to claim 16, wherein the first engagement portion is a slit in the outer tube, and the second engagement portion is a radially outwardly protruding part on the inner tube and the outer tube, the slit extending from the open end, the radially outwardly protruding part being positioned in the slit when the shaft portion is in the accommodated form, the radially outwardly protruding part being axially spaced from the slit when the shaft portion is in the extended form.

18. The medical device according to claim 17, wherein one end of the inner tube is a connected end that is connected to a connecting element and an opposite end of the inner tube is a free end, the flexible portion being provided on the inner tube, the radially outwardly protruding part being positioned closer to the connected end of the inner tube than the flexible portion.

19. The medical device according to claim 17, wherein one end of the inner tube is a connected end that is connected to a connecting element and an opposite end of the inner tube is a free end, the outer tube including an opposite connected end that is opposed to the open end, the flexible portion being provided on the outer tube, the free end of the inner tube being positioned closer to the opposite connected end of the outer tube than the flexible portion when the shaft portion is in the accommodated form.

20. The medical device according to claim 13, wherein the flexible portion:

i) is a portion of the inner tube or the outer tube provided with a spiral-shaped slit or groove; ii) is comprised of a plurality of wires; or iii) is a coil-shaped flexible portion.

21. The medical device according to claim 13, further comprising an expansion body that is configured to change from a radially outwardly expanded position in which the expansion body is radially outwardly expanded with no external force acting on the expansion body and a radially inwardly contracted position in which the expansion body is radially inwardly contracted relative to the radially outwardly expanded position, the expansion body including a proximal portion connected to the outer tube and a distal portion connected to the inner tube so that relative movement of the inner and outer tubes in the axial direction changes the expansion body between the radially outwardly expanded position and the radially inwardly contracted position, the expansion body including a portion extending in a distal direction away from the proximal end of the expansion body and toward the distal end portion of the expansion body, the portion of the expansion body being a radially outwardly expanding portion that expands radially outwardly away from the outer tube when no external force is applied to the expansion body and that axially overlaps the outer tube so that a plane perpendicular to the outer tube and intersecting the outer tube also intersects the radially outwardly expanding portion of the expansion body.

22. A medical device comprising:

an elongate shaft portion;

the shaft portion including an outer tube, and an inner tube that is slidable in an axial direction inside the outer tube;

the outer tube including an open end, the inner tube entering the outer tube and exiting the outer tube by way of the open end;

the inner tube including a flexible portion having lower flexural rigidity than an adjacent portion of the inner tube that is immediately axially adjacent to the flexible portion;

an expansion body including a first connecting portion connected to the outer tube and a second connecting portion connected to the inner tube so that relative movement of the first and second connecting portions causes the expansion body to change between a reference form in which the expansion body is expanded radially outwardly with no external force acting on the expansion body and a contracted form in which the expansion body is contracted radially inwardly so that the expansion body in the contracted form is radially inwardly contracted relative to the expansion body in the reference form; and the shaft portion being configured so that: i) at least a part of the flexible portion of the inner tube is accommodated in the outer tube when the expansion body is in the reference form with no external force acting on the expansion body; and ii) the part of the flexible portion of the inner tube is positioned outside the outer tube and distal of the open end of the outer tube when the expansion body is in the contracted form, whereby the flexible portion is more easily bent when the when the expansion body is in the contracted form than when the expansion body is in the reference form.

23. The medical device according to claim 22, wherein the expansion body includes a proximal end at which is located the first connecting portion that is connected to the outer tube, the expansion body including a portion extending in a distal direction away from the proximal end of the expansion body and toward the second connection portion, the portion of the expansion body being a radially outwardly expanding portion that expands radially outwardly away from the outer tube when no external force is applied to the expansion body and that axially overlaps the outer tube so that a plane perpendicular to the outer tube and intersecting the outer tube also intersects the radially outwardly expanding portion of the expansion body.

* * * * *